(12) United States Patent
Bonrath

(10) Patent No.: US 6,191,313 B1
(45) Date of Patent: *Feb. 20, 2001

(54) PROCESS FOR THE MANUFACTURE OF DIHYDROCITRAL

(75) Inventor: Werner Bonrath, Freiburg (DE)

(73) Assignee: Roche Vitamins Inc., Parsippany, NJ (US)

( * ) Notice: Under 35 U.S.C. 154(b), the term of this patent shall be extended for 0 days.

This patent is subject to a terminal disclaimer.

(21) Appl. No.: 09/280,619

(22) Filed: Mar. 29, 1999

(30) Foreign Application Priority Data

Apr. 7, 1998 (EP) ................................. 98106299

(51) Int. Cl.⁷ .................................... C07C 45/51
(52) U.S. Cl. .................... 568/485; 568/450; 568/449; 568/467; 568/488; 568/490; 568/492
(58) Field of Search ..................... 568/449, 450, 568/467, 485, 488, 490, 492

(56) References Cited

U.S. PATENT DOCUMENTS

| | | | |
|---|---|---|---|
| 3,920,751 | * 11/1975 | Pierre et al. | 260/601 R |
| 4,749,814 | 6/1988 | Chabardes | 568/384 |

FOREIGN PATENT DOCUMENTS

| | | |
|---|---|---|
| 240 431 | 10/1987 | (EP) . |
| 1204754 | 9/1970 | (GB) . |
| 57-203025 | 12/1957 | (JP) . |

OTHER PUBLICATIONS

Price, C.C., et al. *J.A.C.S.* 72:2613–2614 (1950).
*Chem. Abstract* 99, 5873r, vol. 99 (1983).
Khan, N., et al.,*J. Chem. Soc. Perkins Trans.*, 1:1457–1464 (1975).
Lorber, C.Y., et al., *Tetr. Lett.*, 37:6, 853–856 (1996).
Kantam, M.L., et al., *Synthetic Comm.*, 23(1):45–48 (1993).
Erman, M.B., et al., *Tetr. Lett.*,34, 2981–2984 (1976).
Saucy, von G., et al., *Helv. Chim. Acta.*, 42, 1945–1955 (1959).
Meyer, K.H., et al., *Ber. Deutsch Chem. Ges.* 55, 819–823 (1922).
Rupe, von H., et al., *Helv. Chim. Acta.* 9, 672 (1926).

* cited by examiner

*Primary Examiner*—Sreeni Padmanabhan
(74) *Attorney, Agent, or Firm*—Mark E. Waddell; Stephen M. Haracz; Bryan Cave LLP

(57) ABSTRACT

A process for the manufacture of dihydrocitral, a valuable intermediate, through the catalyzed rearrangement of dihydrodehydrolinalool by carrying out the rearrangement in the presence of a molybdenum compound of the general formula $MoO_2X_2$ wherein X signifies an acetylacetonate or halide ion, and a dialkyl or diaryl sulphoxide as the catalyst system, in the presence of an organic acid having a pK value in the range of about 4.0 to about 6.5 and in an aprotic organic solvent.

22 Claims, No Drawings

PROCESS FOR THE MANUFACTURE OF DIHYDROCITRAL

FIELD OF THE INVENTION

The present invention is concerned with a novel process for the manufacture of dihydrocitral by a catalyzed rearrangement reaction.

BACKGROUND OF THE INVENTION

The α,β-unsaturated aldehyde dihydrocitral (E/Z-3,7-dimethyl-2-octen-1-al) is a valuable intermediate.

α,β-Unsaturated carbonyl compounds are generally important intermediates for the manufacture of odorants, vitamins and carotenoids (See, for example, Chem. Ztg. 97, 23–28 (1973) and Ch. VI ("Total Syntheses") in "Carotenoids", Ed. Otto Isler, published by Birkhäuser Basel and Stuttgart (1971)). Their production by acid-catalyzed rearrangement of α-alkynols has already been described in the 1920s by K. H. Meyer and K. Schuster, Ber. deutsch. Chem. Ges. 55:819–823 (1922) and H. Rupe and E. Kambli, Helv. Chim. Acta 9:672 (1926). The isomerization of secondary or tertiary α-alkynols to α,β-unsaturated carbonyl compounds has also generally become known as the Meyer-Schuster or Rupe-Kambli rearrangement. In the case of the rearrangement of a carbonyl compound having a terminal alkynyl group there are obtained aldehydes, otherwise ketones are the rearrangement products:

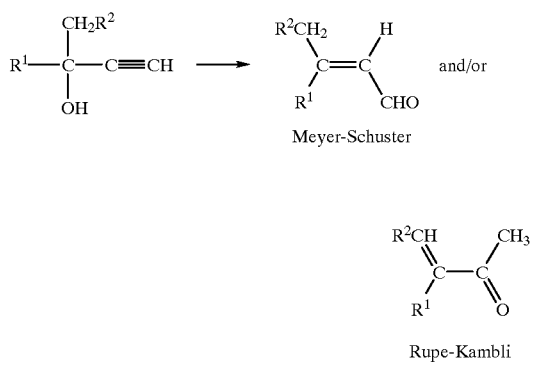

wherein $R^1$ and $R^2$ each signify hydrogen or an aliphatic or aromatic residue.

Depending on the reaction conditions, the rearrangement of dihydrodehydrolinalyl acetate catalyzed by silver or copper ions yields, according to G. Saucy, et al. (Helv. Chim. Acta, 42:1945–1955 (1959)), a mixture of "allene acetate" (1-acetoxy-3,7-dimethyl-octa-1,2-diene) and "diacetate" (1,1-diacetoxy-3,7-dimethyl-2-octene), which can then hydrolyze to dihydrocitral:

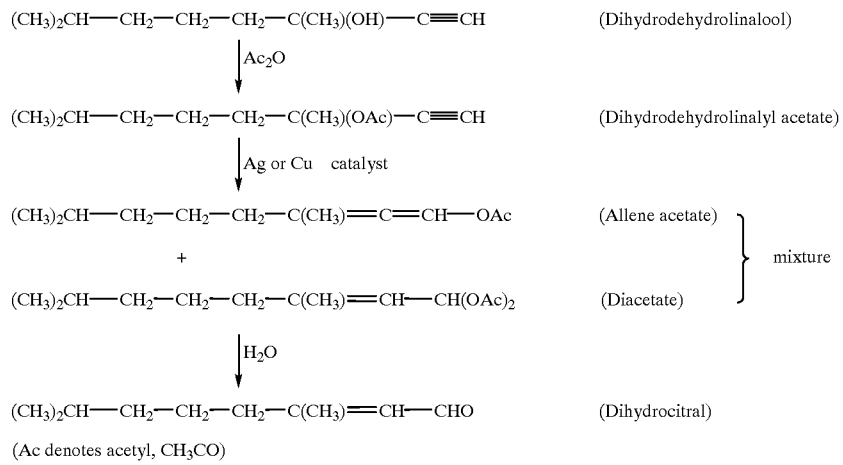

This rearrangement of dihydrodehydrolinalyl acetate is also known as the Saucy-Marbet rearrangement.

Compared with the synthesis of dihydrocitral starting from isoheptanoyl chloride, described by C. C. Price and J. A. Pappalardo, J.A.C.S. 72:2613–2614 (1950), the Saucy-Marbet rearrangement has the advantages of a higher yield, namely 80% in comparison to 20%, and the avoidance of lachrymatory intermediates. Moreover, the use of a silver- or copper-containing catalyst is disadvantageous.

Further known methods for the production of dihydrocitral are the rearrangement of 3-methyl-1-(3-methylbutoxy)-butta-1,3-diene, which is carried out in biphenyl at 350° C., according to Japanese Patent Publication (Kokai) 203025 (1982)/Chem. Abs. 99, 5873r (1983), and the oxidation, which proceeds in 59% yield, of 3,7-dimethyl-oct-2-en-1-ol with silver carbonate on Celite® [Fetizon's reagent; B. C. L. Weedon and co-workers, J. Chem. Soc. Perkin Trans., 1:1457–1464 (1975)]. The high reaction temperature and, respectively, the use of a silver-containing catalyst are disadvantageous.

An interesting variant of the aforementioned Meyer-Schuster rearrangement has been described briefly by C. Y. Lorber and J. A. Osborn in Tetr. Lett., 37:853–856 (1996); this is the rearrangement of methylbutynol to prenal using, a molybdenum catalyst. In this case, methylbutynol is rearranged to prenal in ortho-dichlorobenzene as the solvent in the presence of the catalyst system molybdenyl acetylacetonate, dibutyl sulphoxide and 4-tert.butylbenzoic acid. Although the yield in this rearrangement is indicated to be 97%, the prenal was not isolated from the reaction mixture, but the stated yield was obtained by gas-chromatographical analysis of the crude product. Presumably, it was difficult to work up the reaction mixture in order to isolate prenal.

L. A. Kheifits and co-workers found that dehydrolinalool could be converted into citral only in 28% yield and into 2-hydroxymethyl-1-methyl-3-isopropenylcyclopent-1-ene in 12% yield at 170° C. in a reaction period of 14 hours when a molybdenum catalyst produced from molybdenum oxide and triphenylsilanol was used for the rearrangement (Tetr. Lett., 34:2981–2984 (1976)).

From the above remarks it is evident that the previously known processes for the catalyzed rearrangement of α-alkynols to α,β-unsaturated aldehydes, e.g., dehydrolinalool to citral, have serious disadvantages, which presumably would also apply to the analogous rearrangement of dihydrodehydrolinalool to clihydrocitral.

SUMMARY OF THE INVENTION

The process in accordance with the invention is a process for the manufacture of dihydrocitral by the catalyzed rearrangement of dihydrodehydrolinalool to dihydrocitral, which process comprises carrying out the rearrangement in the presence of a molybdenum compound of the general formula $$MoO_2X_2 \qquad\qquad I$$

wherein X signifies an acetylacetonate or halide ion, and a dialkyl or diaryl sulphoxide as the catalyst system, in the presence of an organic acid having a pK value in the range of about 4.0 to about 6.5 and in an aprotic organic solvent.

The components are added together and mixed. The reaction mixture is heated to a temperature at which the catalytic rearrangement occurs, to provide a resulting mixture. Dihydrocitral can then be obtained from the resulting mixture.

DETAILED DESCRIPTION OF THE INVENTION

The process of the present invention surprisingly achieves a substantial yield of dihydrocitral using a catalyst system which includes the known molybdenum compound molybdenyl acetylacetonate [also known as dioxomolybdenum (VI) acetylacetonate] or a molybdenyl halide.

The molybdenum compound of formula I, i.e., molybdenyl acetylacetonate (conventionally denoted as $MoO_2acac_2$) or a molybdenyl halide of the formula $MoO_2(Hal)_2$ [X=Hal], wherein Hal signifies chlorine or bromine, is in each case a readily obtainable known compound. The molybdenyl halide is preferably molybdenyl chloride, $MoO_2Cl_2$. However, the preferred molybdenum compound of formula I is molybdenyl acetylacetonate.

The dialkyl or diaryl sulphoxide likewise present in the catalyst system is especially a dialkyl sulphoxide, the alkyl groups of which are each straight-chain or branched and contain up to 8 carbon atoms, or a diaryl sulphoxide, the aryl groups of which in each case are optionally substituted phenyl groups. In the latter case, the substituents which may be present are especially $C_{1-4}$-alkyl groups, with the phenyl groups being in each case mono- or multiply-substituted by alkyl. Examples of both types of sulphoxides are dimethyl sulphoxide and dibutyl sulphoxide and, respectively, diphenyl sulphoxide and di(p-tolyl) sulphoxide. Dimethyl sulphoxide is preferably used as the sulphoxide.

As organic acids having a pK value in the range of about 4.0 to about 6.5 there come into consideration, inter alia, optionally halogenated, saturated and unsaturated aliphatic carboxylic acids, e.g., acetic acid (pK value 4.74), propionic acid (4.87), chloropropionic acid (3.98), pivalic acid (5.01) and acrylic acid (4.25); alkanedicarboxylic acids, e.g., adipic acid (4.40); aryl-substituted alkanecarboxylic acids, e.g., phenylacetic acid (4.25); as well as aromatic carboxylic acids, e.g., benzoic acid (4.19) and 4-tert.butyl-benzoic acid (6.50). An organic acid having, a pK value in the range of about 4.25 to about 6.5, especially acrylic acid having the pK value 4.25, is preferably used.

As solvents there can be used in the scope of the present invention in general apolar aprotic organic solvents, especially aliphatic, cyclic and aromatic hydrocarbons, such as, for example, $C_{7-10}$-alkanes, $C_{5-7}$-cycloalkanes, benzene, toluene and naphthalene as well as mixtures of such solvents with one another, e.g., paraffin oil (a mixture of saturated aliphatic hydrocarbons), and polar aprotic organic solvents, especially aliphatic and cyclic esters with up to about 6 carbon atoms, such as, for example, ethyl acetate and butyl acetate and, respectively, ethylene carbonate, propylene carbonate and butyrolactone. Toluene is an especially preferred solvent.

The rearrangement is conveniently effected at temperatures in the range of about 80° C. to about 140° C., preferably at temperatures of about 90° C. to about 120° C.

The amount of molybdenum compound of formula I is conveniently about 0.1–8 mol % based on the amount of dihydrodehydrolinaloo1 (educt) employed. This amount is preferably about 1–7 mol %, particularly about 3–5 mol %.

Furthermore, the weight ratio of dialkyl or diaryl sulphoxide to educt is conveniently from about 0.2:1 to about 1:1; the weight ratio of acid to educt is conveniently from about 0.02:1 to about 0.1:1, preferably about 0.04:1 to about 0.07:1, especially about 0.05:1; and the weight ratio of solvent to educt is conveniently from about 5:1 to about 15:1, preferably about 7:1 to about 10:1.

The process in accordance with the invention can be carried out on an industrial scale very simply by adding the educt, the catalyst system (molybdenum compound of formula I and dialkyl or diaryl sulphoxide) and the organic acid to the solvent and heating the reaction mixture, which normally consists of a suspension because of the different solubilities of the reactants, to the reaction temperature. The reaction mixture is heated to temperatures of from 80° C. to about 140° C., preferably to temperatures of from about 90° C. to about 120° C. Preferably, the reaction mixture is heated to about 100° C. The sequence in which the addition is carried out is not critical, and therefore, for example, the acid or the sulphoxide can be added last.

In order to determine the course of the reaction, samples of the reaction mixture can be withdrawn and analysed according to known methods, e.g., thin-layer chromatography or gas chromatography. After completion of the reaction, the reaction period normally being up to about 20 hours, preferably up to about 7 hours, the working up can be effected by conventional procedures of organic chemistry. Typically, the mixture is filtered and the dihydrocitral product is isolated from the filtrate by evaporation. For purification of the product, the crude material can, for example, be distilled.

The process in accordance with the invention is illustrated by the following Examples:

EXAMPLE 1

Various Rearrangement Experiments Under the Same Conditions 6.24 g (39.62 mmol) of dihydrodehydrolinalool (hereinafter "DDLL"), 2.31 g (29.67 mmol) of dimethyl sulphoxide (hereinafter "DMSO"), 0.65 g (1.98 mmol) of molybdenyl acetylacetonate (hereinafter "MoO$_2$acac$_2$") and 1.05 g (14.58 mmol) of acrylic acid in 50 ml of toluene were placed in a 100 ml sulphonation flask provided with a thermometer, stirrer and reflux condenser. Subsequently, the mixture was heated to 100° C. During this a green-brown solution formed from the initially red-brown suspension. For determining the course of the reaction, samples were removed and analyzed by thin-layer chromatography (TLC) or gas chromatography (GC). After completion of the reaction (17 hours reaction time) the mixture was worked up by cooling to room temperature, filtration over 10 g of silica gel, rinsing the silica gel with 100 ml of toluene and finally concentrating at 40° C. and 70 mbar (7 kPa) pressure. In this manner there were obtained 7.61 g of crude product which, according to a content determination by GC with an internal standard, consisted of 4.69% of unreacted DDLL (0.37 g, 5.93 mol. % of the 6.24 g used) and of 61.05% of the desired dihydrocitral (4.78 g, 76.61 mol. % yield). This gives a percentage ratio of dihydrocitral (hereinafter "DHC") to DDLL of 81.43% [(g DHC÷g reacted DDLL, 5.87 g)×100].

The above experiment (No.1) was repeated three times with unchanged amounts and reaction and working up conditions. The results compiled in the following Table were obtained:

TABLE

| Experiment | Reacted | Yield in mol. % | | Yield in g | | Percent ratio |
|---|---|---|---|---|---|---|
| No. | DDLL | DDLL | DHC | DDLL | DHC | DHC:DDLL |
| 2 | 5.87 g | 11.54 | 74.19 | 0.72 | 4.63 | 83.88% |
| 3 | 5.00 g | 19.71 | 67.26 | 1.23 | 4.20 | 84.00% |
| 4 | 5.44 g | 12.82 | 71.28 | 0.80 | 4.45 | 81.80% |

EXAMPLE 2

Rearrangement Using Butyl Acetate as the Solvent

As described in Example 1, a suspension of 6.24 g. (39.62 mmol) of DDLL, 2.31 g. (29.67 mmol) of DMSO, 0.65 g. (1.98 mmol) of MoO$_2$acac$_2$ and 1.05 g. (14.58 mmol) of acrylic acid in 50 ml of butyl acetate was heated to 100° C. During this a green solution formed from the initially red-brown suspension. After a reaction period of 17 hours the mixture was cooled to room temperature and the reaction solution was filtered over 10 g. of silica gel. The silica gel was rinsed with 100 ml of toluene and the solvent was evaporated at 40° C. and 70 mbar (7 kPa). In this manner there were obtained 10.2 g. of crude product which, according to a content determination by GC with an internal standard, consisted of 41.12% of DHC and had no unreacted DDLL. The content of DHC was 4.19 g. (67.22% yield).

From the foregoing description, one skilled in the art can ascertain the essential characteristics of this invention, and without departing from the spirit and scope thereof, can make various changes and modifications. Preferred embodiments set forth by way of illustration are not intended as limitations on the variations possible in practising the present invention.

What is claimed is:

1. A process for the manufacture of dihydrocitral by the catalytic rearrangement of dihydrodehydrolinalool to dihydrocitral, which process comprises carrying out the rearrangement of dihydrodehydrolinalool in the presence of a molybdenum compound of the general formula MoO$_2$X$_2$ wherein X is an acetylacetonate or a halide ion, a sulphoxide which is selected from the group consisting of dialkyl sulphoxides and diaryl sulphoxides and an organic acid having, a pK value from about 4.0 to about 6.5, in an aprotic organic solvent to provide dihydrocitral.

2. The process according to claim 1, wherein the molybdenum compound of claim 1 is selected from molybdenyl acetylacetonate and molybdenyl chloride.

3. The process according to claim 2, wherein the molybdenum compound is molybdenyl acetylacetonate.

4. The process according to claim 1, wherein the sulphoxide is selected from the group consisting of dimethyl sulphoxide, dibutyl sulphoxide, diphenyl sulphoxide and di(p-tolyl) sulphoxide.

5. The process according to claim 4, wherein the sulphoxide is dimethyl sulphoxide.

6. The process according claim 1, wherein the organic acid is selected from the group consisting of saturated aliphatic carboxylic acids, unsaturated aliphatic carboxylic acids, halogenated saturated aliphatic carboxylic acids, halogenated unsaturated aliphatic carboxylic acids, alkanedicarboxylic acids, aryl-substituted alkanecarboxylic acids, and aromatic carboxylic acids.

7. The process according to claim 6, wherein the organic acid is selected from the group consisting of acetic acid, propionic acid, chloropropionic acid, pivalic acid, acrylic acid, adipic acid, phenylacetic acid, benzoic acid, and 4-tert.butyl-benzoic acid.

8. The process according to claim 7, wherein the organic acid is acrylic acid.

9. The process according to claim 1, wherein the solvent is an aprotic organic solvent.

10. The process according to claim 9, wherein the solvent is selected from the group consisting of aliphatic hydrocarbons, cyclic hydrocarbons, aromatic hydrocarbons, mixtures of any of two or more of said hydrocarbons with one another, aliphatic esters having up to about 6 carbon atoms, and cyclic esters having up to about 6 carbon atoms.

11. The process according to claim 10, wherein the solvent is selected from the group consisting of $C_{7-10}$-alkanes, $C_{5-7}$-cycloalkanes, benzene, toluene, naphthalene, paraffin oil, ethyl acetate, butyl acetate, ethylene carbonate, propylene carbonate and butyrolactone.

12. The process according to claim 1, wherein the solvent is toluene.

13. The process according to claim 11, wherein the rearrange net is carried out at a temperature from about 80° C. to about 140° C.

14. The process according to claim 13, wherein the rearrangement is carried out at a temperature from about 90° C. to about 120° C.

15. The process according to claim 1, wherein the amount of the molybdenum compound is from about 0.1 to about 8 mol % based on the amount of dihydrodelhydrolinalool.

16. The process according to claim 15, wherein the amount of the molybdenum compound is from about 1 to about 7 mol % based on the amount of dihydrodehydrolinalool.

17. The process according to claim 16, wherein the amount of the molybdenum compound is from about 3 to about 5 mol % based on the amount of dihydrodehydrolinalool.

18. The process according to claim 1, wherein the weight ratio of the sulphoxide to dihydrodehydrolinalool is from about 0.2:1 to about 1:1, the weight ratio of the organic acid to dihydrodehydrolinalool is from about 0.02:1 to about 0.1:1 and the weight ratio of the solvent to dihydrodehydrolinalool is from about 5:1 to about 15:1.

19. The process according to claim 18, wherein the weight ratio of the organic acid to dihydrodehydrolinalool is from about 0.04:1 to about 0.07:1.

20. The process according to claim 19, wherein the weight ratio of the organic acid to dihydrodehydrolinalool is about 0.05:1.

21. The process according to claim 18, wherein the weight ratio of the solvent to dihydrodehydrolinalool is from about 7:1 to about 10:1.

22. A process for the manufacture of dihydrocitral by the catalytic rearrangement of dihydrodehydrolinalool to dihydrocitral, comprising:

(a) mixing dihydrodehydrolinalool, a molybdenum compound of the general formula $MoO_2X_2$ wherein X is an acetylacetonate or halide ion, a dialkyl or diaryl sulphoxide, and an organic acid having a pK value of from about 4.0 to about 6.5 and an aprotic organic solvent, to provide a reaction mixture;

(b) heating the reaction mixture to a temperature at which the catalytic rearrangement reaction occurs, to provide a resulting mixture; and (c) obtaining the dihydrocitral from the resulting mixture.

* * * * *

UNITED STATES PATENT AND TRADEMARK OFFICE
CERTIFICATE OF CORRECTION

PATENT NO.   : 6,191,313 B1
DATED        : February 20, 2001
INVENTOR(S)  : Werner Bonrath, et al.

It is certified that error appears in the above-identified patent and that said Letters Patent is hereby corrected as shown below:

<u>Column 6,</u>
Line 40 (line 1 of claim 12), change "1" to -- 11 --;
Line 13 (line 1 of claim 13), change "11" to -- 1 --;
Line 13 (line 2 of claim 13), change "rearrange net" to -- rearrangement --.

Signed and Sealed this

Twenty-fifth Day of September, 2001

Attest:

*Nicholas P. Godici*

NICHOLAS P. GODICI
*Attesting Officer*   *Acting Director of the United States Patent and Trademark Office*